US007575365B2

(12) United States Patent
Jung

(10) Patent No.: US 7,575,365 B2
(45) Date of Patent: Aug. 18, 2009

(54) VISCOSITY CONTROL OF PARTICLE FORMATION BY ADJUSTING AGITATION SPEED

(75) Inventor: Philip O. Jung, Mobile, AL (US)

(73) Assignee: UOP LLC, Des Plaines, IL (US)

( * ) Notice: Subject to any disclaimer, the term of this patent is extended or adjusted under 35 U.S.C. 154(b) by 165 days.

(21) Appl. No.: 11/924,634

(22) Filed: Oct. 26, 2007

(65) Prior Publication Data

US 2009/0107196 A1 Apr. 30, 2009

(51) Int. Cl.
*B01F 13/06* (2006.01)
*C05C 1/00* (2006.01)

(52) U.S. Cl. .......................... 366/348; 366/601; 71/59; 71/64.08; 264/8; 264/9

(58) Field of Classification Search ..................... 366/2, 366/3, 142, 153.1, 348, 601; 264/8, 9, 40.3; 71/59, 63, 64.03, 64.06, 64.08, 64.1
See application file for complete search history.

(56) References Cited

U.S. PATENT DOCUMENTS 3,617,235 A 11/1971 Friestad et al.
3,630,495 A * 12/1971 Carroll ...................... 366/343
3,856,269 A 12/1974 Fothergill et al.
4,013,504 A 3/1977 Morris
4,323,386 A 4/1982 Heggebo et al.
4,363,742 A * 12/1982 Stone ..................... 252/182.1
4,436,431 A * 3/1984 Strong et al. ................. 366/17
4,705,535 A 11/1987 Lipp
5,660,468 A * 8/1997 Okajima et al. ............ 366/306
7,175,684 B1 * 2/2007 Kweeder et al. .............. 71/59
2009/0107196 A1 * 4/2009 Jung ............................ 71/59

FOREIGN PATENT DOCUMENTS

DE 2355660 A1 11/1973
GB 1481038 11/1974
GB 2180773 A * 4/1987
SE 70119 1/1929

* cited by examiner

*Primary Examiner*—Charles E Cooley
(74) *Attorney, Agent, or Firm*—Mark Goldberg

(57) ABSTRACT

A method of prilling or spray drying comprising calculating and controlling the viscosity of a shear-thinnable fluid stream at a particle-forming section of a dispersion device. The method comprises measuring the static head of fluid in the dispersion device, providing a pressurized blanket of inert gas over the fluid, mechanically agitating the fluid in the dispersion device, calculating the viscosity at the particle-forming section and controlling the viscosity by adjusting the speed of mechanical agitation.

19 Claims, 3 Drawing Sheets

VISCOSITY CONTROL OF PARTICLE FORMATION BY ADJUSTING AGITATION SPEED

FIELD OF THE INVENTION

This invention relates to an method of particle formation. More particularly, it relates to a method of prilling or spray-drying a shear-thinnable mixture by calculating and controlling the viscosity of the mixture just prior to formation of particles.

BACKGROUND OF THE INVENTION

Prilling and spray drying are used widely in the production of spherical particles having uniform size and physical characteristics. Prilling is particularly useful in the fertilizer industry. The advantages of prilling are well known in the art, and include: high percentage of desired product size and thus little recycle, reduced moisture content leading to reduced drying, and excellent sphericity. One frequent problem in prilling relates to processing thick mixtures resulting from a high concentration of a non-melting component in a melt. It may become difficult to flow the resulting thick mixture through conventional prilling systems.

U.S. Pat. No. 7,175,684 addresses this problem by effecting shear thinning by mechanical agitation in the prill head. The thinned mixture can be prilled through a modified prill head in a conventional manner. The features and disclosures of the '684 patent are incorporated herein in their entirety by reference thereto.

Other approaches have been disclosed to solve this problem of a thick mixture. For example, methods have been devised to manage this complication by minimizing reaction time. GB 1,481,038 teaches a simple concept of severely limiting the processing time (the period between the time the melt is fed into the mixer to the time the drops are discharged from the prilling apparatus) to 10 seconds or less so that the mixture can be prilled before any detrimental effects develop. U.S. Pat. No. 3,617,235 teaches the use of larger-sized solid particles to slow reaction prior to prilling. U.S. Pat. No. 4,323,386 teaches a method of managing the addition of reagent, delaying full addition of ingredients until just prior to prilling, again to preclude reactions. U.S. Pat. No. 3,856,269 discloses a mixing apparatus to facilitate prilling by providing very rapid but adequate mixing of fertilizer ingredients prior to prilling in a standard perforated spinning bucket. These methods add cost and complication to the prilling operation, however, by requiring feedstocks with narrow specifications or the expense of engineering the production system to achieve very brief residence times, or else compromising a desirable property by curtailing the extent of reaction.

Another approach to prilling thick mixtures is to provide equipment that will force the flow of the slurry. SE 70,119 teaches a vertical screw machine to blend ammonium nitrate melt with ammonium sulfate solid; the pressure developed by the screw and static head is supplemented by injection behind the spray nozzle. DE 2,355,660 teaches a prill head incorporating a stirrer-impeller mechanical device similar to a centrifugal pump whereby the slurry is introduced at the center and forced under pressure out holes on the circumference of the prilling disk. These mechanical devices involve considerable cost in construction, and the abrasive nature of fertilizer slurry will wear the close clearances necessary for efficient pumping with resulting significant maintenance expense.

Spray drying using a two-fluid nozzle is disclosed in U.S. Pat. No. 4,705,535. The nozzle is adjustable to provide a substantially constant mixing energy for atomization of the liquid. Mixing energy is determined from the mass flow of gas and of liquid to the nozzle, gas pressure at the point of feed to the nozzle, and pressure in the vessel into which the spray is discharged. This reference is silent, however, with respect to modification of characteristics of the fluid to the nozzle.

U.S. Pat. No. 4,013,504 teaches a spray-drying apparatus comprising a high-speed rotary atomizing head having circumferentially spaced discharge orifices and spiral vanes on the exterior portion of the head. A film of slurry from the orifices flowing over the vanes is subjected to high shear stresses which materially improve the viscosity of the product and disperses particles in an efficient manner. This reference acknowledges the problem of viscosity and use of shear, but does not disclose control of flow through the orifices.

The present invention avoids the higher costs, maintenance and complications of the known art as well as the disadvantages of approaches based on curtailed reactions, and builds on the shear-thinning feature of U.S. Pat. No. 7,175,684.

SUMMARY OF THE INVENTION

The present invention broadly comprises a method of calculating and controlling the viscosity of a shear-thinnable fluid stream at a particle-forming section of a dispersion device by providing a measured static head of shear-thinnable fluid within the dispersion device, providing a pressurized blanket of inert gas over the fluid at a measured gas pressure, mechanically agitating the fluid in the dispersion device at a measured agitation speed; calculating the viscosity of the agitated fluid, and controlling the viscosity as the fluid passes through the particle-forming section by adjusting the agitation speed.

A more specific embodiment comprises a method of calculating and controlling the viscosity of a shear-thinnable fluid stream at a prill head by providing a measured static head of shear-thinnable liquid within the prill head, providing a pressurized blanket of inert gas over the liquid at a measured gas pressure, mechanically agitating the liquid in the prill head at a measured agitation speed, calculating the viscosity of the agitated liquid as it passes through the particle forming section, and controlling the viscosity of the liquid inside the particle forming section by adjusting the agitation speed.

An alternative embodiment comprises a method of calculating and controlling the viscosity of a shear-thinnable fluid stream in a spray nozzle by providing a measured static head of shear-thinnable fluid within the nozzle, providing a pressurized blanket of inert gas over the fluid at a measured gas pressure, mechanically agitating the fluid in the nozzle at a measured agitation speed, calculating the viscosity of the agitated fluid, and controlling the viscosity of the fluid by adjusting the agitation speed.

A specific use of the invention comprises addition of ammonium sulfate to an ammonium nitrate melt, reaction of the consequent mixture to form a double salt ammonium sulfate nitrate, and prilling the resultant shear-thinnable melt slurry in the present process to yield prills having excellent strength, sphericity and storage properties.

DETAILED DESCRIPTION OF THE PREFERRED EMBODIMENTS

The term "prilling" as used herein refers to formation of solid particles or "prills" in an open tower via solidification as droplets fall from a prill head. A prill head is the apparatus at the top of a prill tower which divides the molten material into the streams from which the prills form.

The term "spray-drying" as used herein refers to dispersal of a solution or slurry into a stream of hot gas in a manner to vaporize a volatile solvent and produce residual solid particulates. Spray-drying is distinguished from prilling by the substantial presence of a volatile solvent in the solution or slurry.

The term "shear-thinning" as used herein refers to the phenomena of decreasing viscosity with increasing shear rate. Not all mixtures exhibit shear-thinning and it cannot be predicted which mixtures will and which will not possess this behavior.

The term "shear-thinnable mixture" as used herein refers to a system comprising at least two components in which the first component is or forms a molten melt and at least one second component which in combination results in a mixture which has high viscosity and demonstrates shear-thinning behavior. A "shear-thinnable mixture" may include a melt slurry wherein the molten limited meltability and/or limited solubility mixture contains solid particles.

Figure 1:
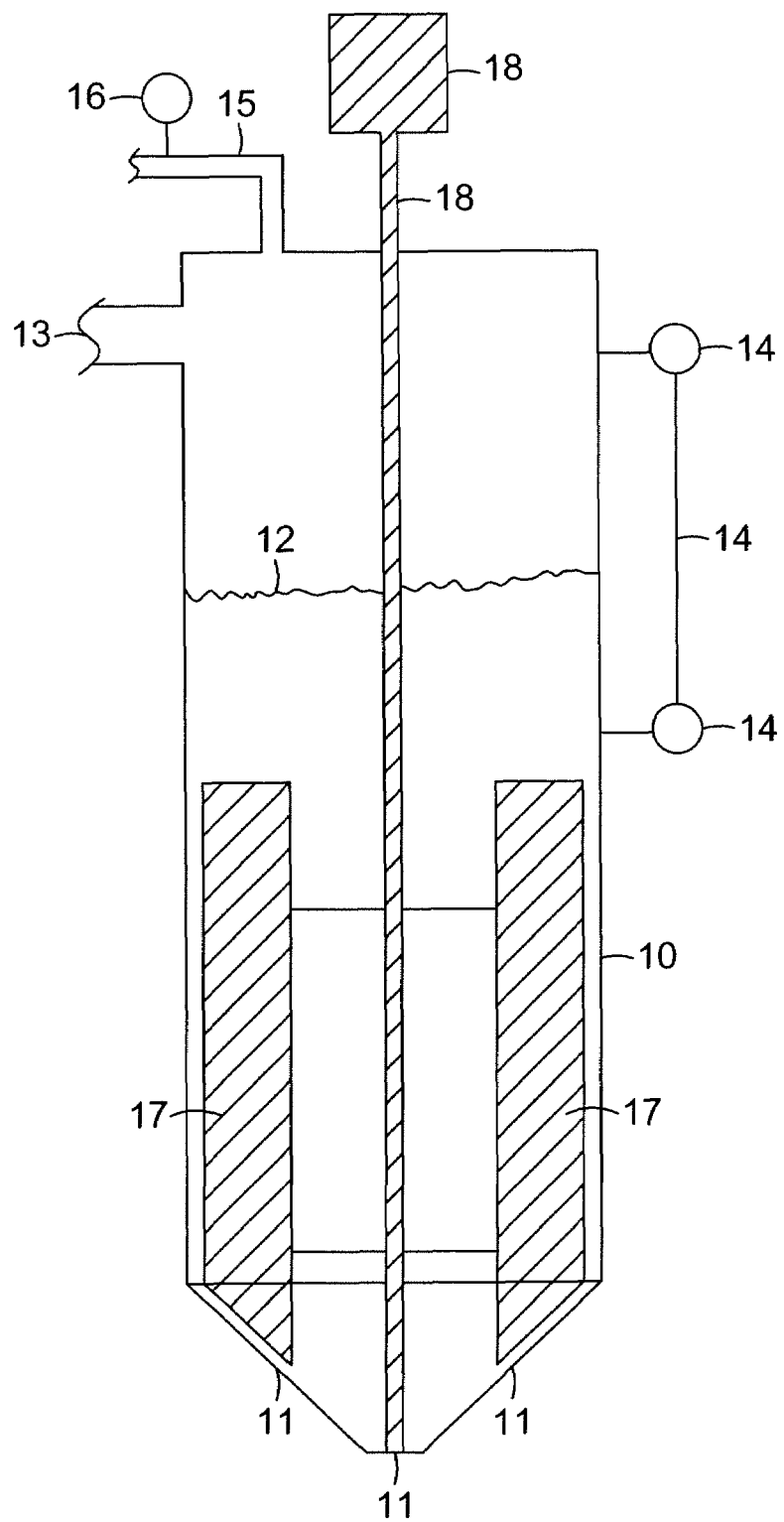
FIG. 1 shows a broad schematic representation of the present invention.
Figure 2:
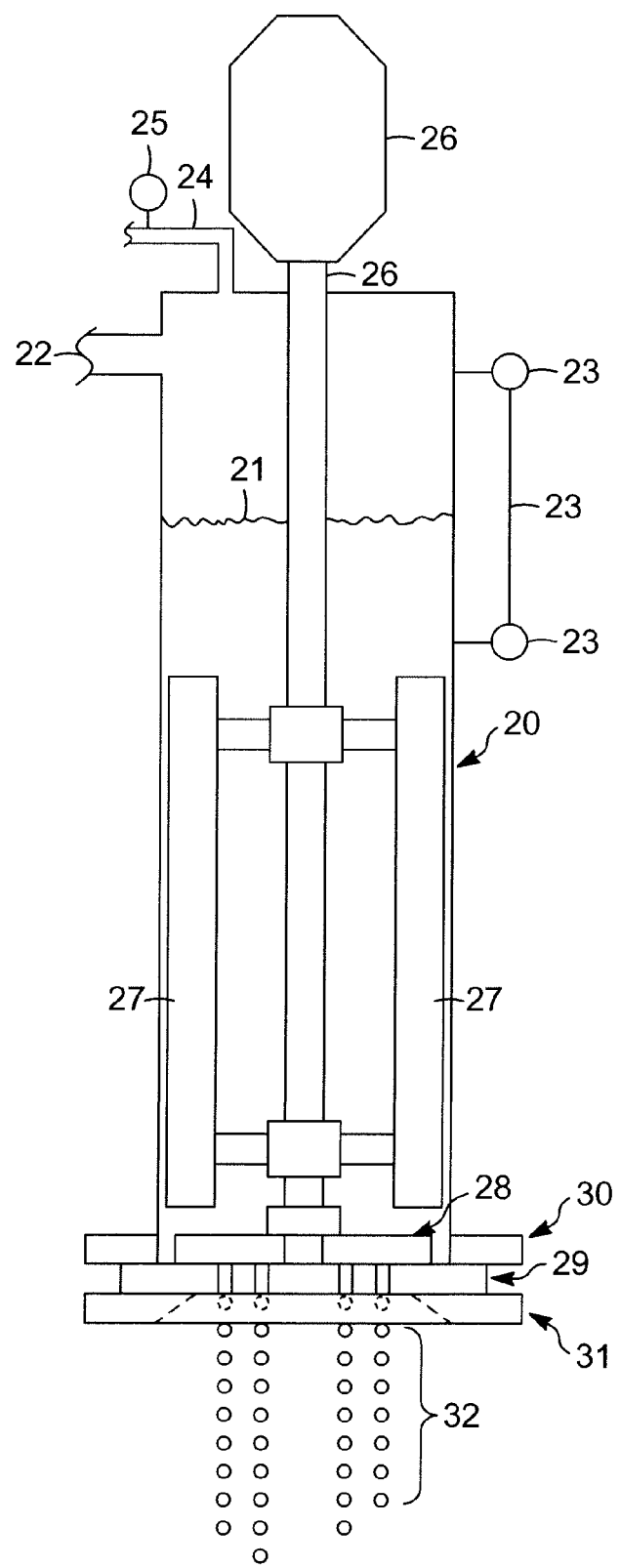
FIG. 2 shows a prill head design useful in the practice of the invention.
Figure 3:
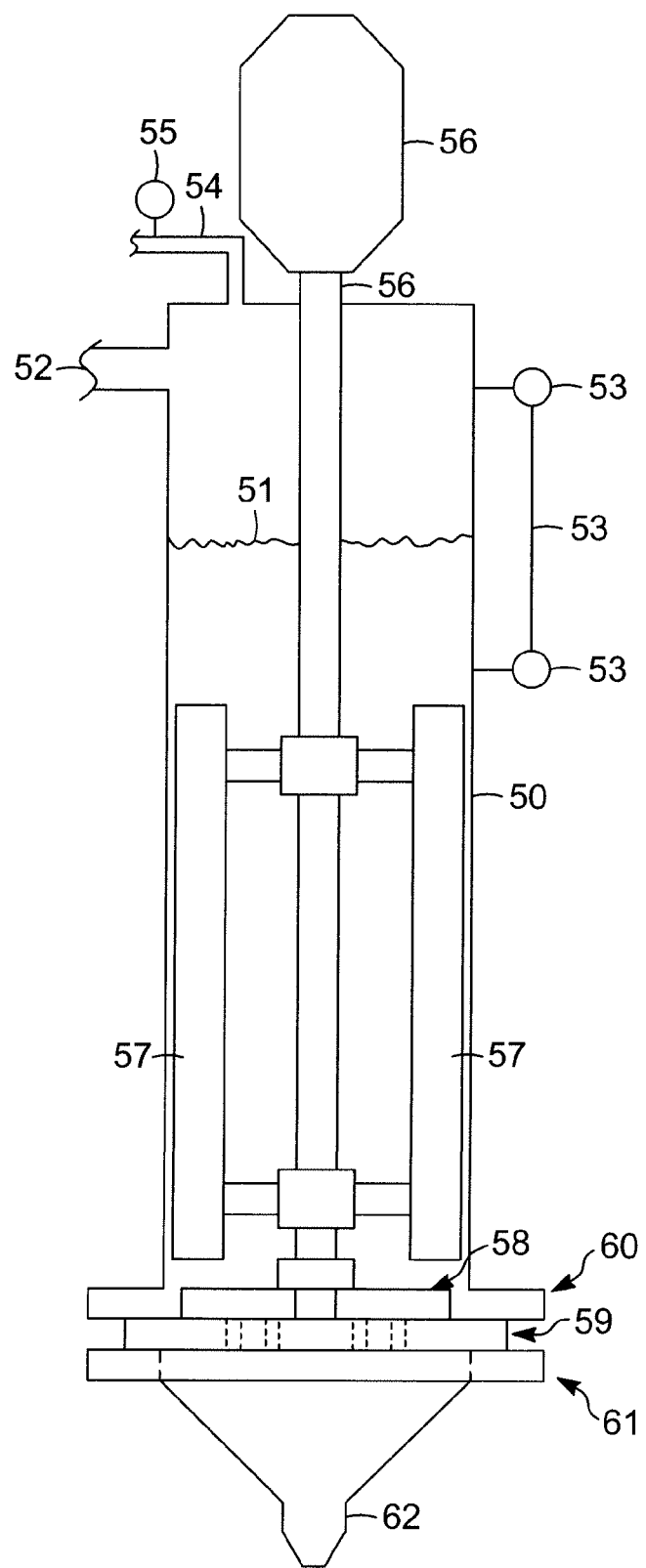
FIG. 3 shows a spray-drying apparatus useful in the practice of the invention.

The schematic representation in FIG. 1 can generally be considered to embrace a cross-section of either the prilling or the spray-drying embodiment of the invention. A dispersion device 10 contains a fluid from which particles are to be formed as well as a pressure gauge, a shear-thinning apparatus and a particle-forming section. Particles are formed from section 11, which may be configured in any suitable manner either for prill formation or for spray drying as described elsewhere herein. The fluid, having a surface represented by 12, enters the apparatus through conduit 13. The level of the fluid surface in the device is controlled between upper and lower limits established by level gauge 14 between the entry conduit and the shear-thinning apparatus. An inert gas, for example nitrogen, is provided through conduit 15 and determines pressure in the apparatus through pressure gauge 16. Shear-thinning of the fluid is effected by an apparatus comprising agitation device 17 which is rotated within the device by motive device and shaft 18. The agitation and motive devices may be of any suitable configuration described herein or generally known in the art; it is within the scope of the invention that the dispersion device can be a rotating bucket and the agitation device 17 is stationary.

The viscosity of the shear-thinned mixture at the particle-forming section is important to the rate and particle characteristics of the prilling or spray-drying operation. This viscosity can be calculated and thus controlled by backward solution of the classic Fanning or Darcy equations coupled with Bernoulli's equation, considering the static head as measured by level gauge 14 as determined by the flow rate of material entering through conduit 13, the pressure of the inert gas as measured by pressure gauge 16, and the shear-thinning agitation effected by agitation device 17, and the configuration and resulting hydraulic characteristics of the particle-forming section; the Example described hereinafter shows the results of such calculation. For a given prilling or spray-drying operation, a viscosity increase must be compensated by an increase in gas pressure or liquid level to maintain a given rate of particle formation; the viscosity then may be adjusted by varying the shear-thinning agitation. Depending on the specific characteristics of the desired particles and the type of viscometer used in measurement, the viscosity generally should be in the range of from about 5 to about 6000 cp (centipoises), and more usually within the range of from about 10 to about 600 cp.

FIG. 2 is a schematic illustration of a cross-section of a prilling embodiment of the invention. A prill head 20 contains a fluid from which particles are to be formed as well as a pressure gauge, a shear-thinning apparatus, and a prill-forming section. The fluid, having a surface represented by 21, enters the apparatus through conduit 22. The level of the fluid surface in the device is controlled between upper and lower limits established by level gauge 23 between the entry conduit and the shear-thinning apparatus. An inert gas, for example nitrogen, is provided through conduit 24 and determines pressure in the apparatus through pressure gauge 25. Motive device and shaft 26 are, e.g., a variable-frequency-drive motor which rotate the shear-thinning apparatus comprising high-shear mixing blades 27 and optional floating wiper 28. The floating wiper provides final high-shear agitation for small prills; very small prills require that the blade 27 has zero clearance above prill-head sizing device 29 in order to wipe the plate. The prill-head sizing device 29, or prill plate, is held in place by prill-head flange 30 and head-holding flange 31, yielding prills 32.

In all embodiments of the agitated prill head, the prill holes should be spaced sufficiently apart from each other to preclude the descending streams and/or prills from touching one another and coalescing. Prill hole diameters may be any size commonly practiced in the art. Prill hole diameters of about 2.0 to about 4.0 mm are particularly useful in the inventive process and apparatus. Smaller prill hole diameters, of less than 2.0 mm, may be used in an agitated prill head and may utilize surface-wiping blades to wipe the prill plate.

FIG. 3 is a schematic illustration of a cross-section of a spray-drying embodiment of the invention. A spray-nozzle body 50 contains a fluid from which particles are to be formed as well as a pressure gauge, a shear-thinning apparatus, and a spray-granulation section. The fluid, having a surface represented by 51, enters the apparatus through conduit 52. The level of the fluid surface in the device is controlled between upper and lower limits established by level gauge 53 between the entry conduit and the shear-thinning apparatus. An inert gas, for example nitrogen, is provided through conduit 54 and determines pressure in the apparatus through pressure gauge 55. Motive device and shaft 56 are, e.g., a variable-frequency-drive motor which rotate the shear-thinning apparatus comprising high-shear mixing blades 57 and final high-shear agitator 58. A restrictor 59 is held in place by body flange 60 and head-holding flange 61, sending the sheared fluid to a spray head, or a pressurized nozzle assembly 62.

In spray drying, the fluid from the nozzle is dispersed into a stream of hot gas in a mist of fine droplets. Moisture is vaporized from the droplets to leave residual particles of dry solid which are separated from the gas stream. The flow of fluid and gas may be cocurrent, countercurrent or a combination of both. Further details of spray drying may be found in Perry, J. H. et al., CHEMICAL ENGINEERS' HANDBOOK, $7^{th}$ ed., McGraw-Hill Book Co., Inc., New York (1997), or in Masters, K., SPRAY DRYING, AN INTRODUCTION TO PRINCIPLES, OPERATIONAL PRACTICE AND APPLICATIONS, $2^{nd}$ ed., G. Godwin Ltd., London, J. Wiley & Sons, New York (1976), both of which are incorporated herein by reference.

Generally, any mixture of components that yields a shear-thinnable mixture may be used in the inventive method. The invention is particularly useful in forming prills or granules of ammonium sulfate nitrate, the double salt of ammonium sulfate and ammonium nitrate As the molten first component, ammonium nitrate is most preferred. Other suitable molten first components include urea and ammonium phosphates. Suitable second components may include any material which results in a viscous and shear-thinnable mixture when added to the molten first component. The second component may or may not be fully meltable and/or soluble in the molten first component. As the second component, ammonium sulfate is most preferred. Useful ammonium sulfate is commercially available from Honeywell International Inc., Hopewell, Va., USA. Other suitable second components include potassium chloride. Other materials can be added to the shear-thinnable mixture if desired as long as they do not adversely affect prilling. For example, possible third components include micronutrients such as iron sulfate, magnesium sulfate, boron salts, and anti-caking agents.

Temperature restrictions on the reaction are dictated by the components used. One needs to uses a temperature range in which the first component melts without problems of decomposition or deflagration. When using ammonium nitrate, the minimum temperature is about 180° C. (the melting point of ASN) and a safe maximum reasonable handling temperature is about 200° C. Preheating the second component before addition to the molten first component is useful in mixtures where the heat of reaction is important, and is generally desirable due to heat transfer.

Generally, addition of water to a mixture to be prilled is minimized to allow solidification of the prills without the need for removal of excess solvent. The water addition aids melting and suppresses fuming of ammonium nitrate. Addition of water to the molten mixture is preferred to be no more than about 2.0 weight percent (wt-%) and is preferably less than or equal to about 1.0 wt-% and more preferably less than or equal to about 0.5 wt-%. Addition of water from about 2 to about 6 wt-% is possible; however, it detrimentally impacts prill strength, and requires the prills to be dried.

One of the benefits of the inventive process is that it allows sufficient reaction time to develop advantageous properties in the product. For instance, pure ammonium nitrate prills are problematic for several reasons: 1) storage problems result from its hygroscopic nature; 2) a phase transition at 32° C. can cause the prills to break apart as the temperature fluctuates ("sugaring"); and 3) it is an oxidizer. In contrast, using ammonium nitrate and ammonium sulfate in the inventive process results in a double salt ASN product that has vanishingly little unreacted ammonium nitrate. This product possesses many favorable properties including: 1) reduced hygroscopic problems; 2) no "sugaring"; and 3) ASN is not an oxidizer.

EXAMPLE

A spreadsheet was developed applying the classic Fanning equation coupled with Bernoulli's equation as applied to the following parameters to calculate the viscosity of a shear-thinned mixture at a prill head:

Prill head:

| | |
|---|---|
| Number of machined holes | 100 |
| Estimated blocked holes | 11 |
| Number of operating holes | 89 |
| Diameter of holes | 3.6 mm |
| Cross-sectional area of each hole | 10.18 mm$^2$ |
| Thickness of prill head at hole | 1.9 mm |
| Entrance of fluid to hole | sharp-edged |
| Entry coefficient | 0.5 |
| Fluid properties: | |
| Specific gravity at operating temperature | 1.6 |
| Operating conditions: | |
| Height of liquid in shearing device | 0.67 meters |
| Pressure above liquid in shear device | 11.0 kPa |
| Pressure at prill head | 2.198 meters of water |
| Pressure inside prilling tower | −10 cm of water |
| Flow rate of liquid to prilling head | 0.2196 m$^2$/minute |
| Calculated conditions: | |
| Differential pressure across prill head | 2.30 meters of water |
| Flow rate of liquid to prilling head | 0.2196 m$^3$/minute |
| Mass flow to prilling head | 350.6 kg/minute |
| Mass flow to prilling head | 21,038 kg/hour |
| Average flow through each hole | 3.9397 kg/minute |
| Average flow through each hole | 236.38 kg/hour |
| Average flow through each hole | 0.002467 m$^3$/minute |
| Velocity through prilling hole | 248.4 meters/minute |
| Velocity through prilling hole | 4.14 meters/second |
| Pressure drop: | |
| Velocity pressure inside prilling hole | 0.872 meters of water |
| Pressure drop from prilling hole length | 0.991 meters of water |
| Total pressure drop with orifice entrance | 2.30 meters of water |
| Total pressure drop available | 2.30 meters of water |
| Viscosity of prilling fluid | 48.7 cp |

The invention claimed is:

1. A method of calculating and controlling the viscosity of a shear-thinnable fluid stream at a particle-forming section of a dispersion device by:
    a) providing a measured static head of shear-thinnable fluid within the dispersion device;
    b) providing a pressurized blanket of inert gas over the fluid at a measured gas pressure;
    c) mechanically agitating the fluid in the dispersion device at a measured agitation speed;
    d) calculating the viscosity of the agitated fluid; and
    e) controlling the viscosity at the particle-forming section by adjusting the agitation speed.

2. The method of claim 1 wherein the dispersion device is a prill head and the particles are prills.

3. The method of claim 1 wherein the shear-thinnable liquid is formed by providing a molten first component, mixing at least one second component with the first component, and reacting the components at a temperature and for a time sufficient to form a mixture having a viscosity which decreases with increasing shear rate.

4. The method of claim 3 wherein the shear-thinnable mixture is a melt slurry.

5. The method of claim 1 wherein the shear-thinnable liquid comprises no more than about 2 weight percent water.

6. The method of claim 1 wherein the dispersion device is a spray nozzle.

7. The method of claim 6 wherein the liquid is a slurry.

8. A method of calculating and controlling the viscosity of a shear-thinnable fluid stream at a prill head by:

a) providing a measured static head of shear-thinnable liquid within the prill head;

b) providing a pressurized blanket of inert gas over the liquid at a measured gas pressure;

c) mechanically agitating the liquid in the prill head at a measured agitation speed;

d) calculating the viscosity of the agitated liquid; and e) controlling the viscosity of the liquid at the prill head by adjusting the agitation speed.

9. The method of claim 8 wherein the shear-thinnable liquid is formed by providing a molten first component, mixing at least one second component with the first component, and reacting the components at a temperature and for a time sufficient to form a mixture having a viscosity which decreases with increasing shear rate.

10. The method of claim 9 wherein the shear-thinnable mixture is agitated in the prill head under conditions such that the entire liquid volume in the prill head is swept by the agitator to shear-thin the shear-thinnable mixture.

11. The method of claim 9 wherein the shear-thinnable mixture is a melt slurry.

12. The method of claim 9 wherein the first component is ammonium nitrate and the second component is ammonium sulfate.

13. The method of claim 9 wherein the shear-thinnable mixture further comprises micronutrients.

14. The method of claim 9 wherein the shear-thinnable mixture comprises no more than about 2 weight percent water.

15. The method of claim 8 wherein the prill head is one selected from the group comprising a rotating bucket with a stationary blade, a stationary bucket with rotating scrappers and blades, and an agitated pressurized nozzle assembly.

16. The method of claim 8 wherein the prill head is wiped with surface-wiping blades.

17. A method of calculating and controlling the viscosity of a shear-thinnable fluid stream in a spray nozzle by:

a) providing a measured static head of shear-thinnable fluid within the nozzle;

b) providing a pressurized blanket of inert gas over the fluid at a measured gas pressure;

c) mechanically agitating the fluid in the nozzle at a measured agitation speed;

d) calculating the viscosity of the agitated fluid; and e) controlling the viscosity of the fluid by adjusting the agitation speed.

18. The method of claim 17 wherein the liquid is a slurry.

19. The method of claim 17 wherein the nozzle is one selected from the group comprising a rotating bucket with a stationary blade, a stationary bucket with rotating scrappers and blades, and an agitated pressurized nozzle assembly.

* * * * *